US009046618B2

(12) United States Patent
Hess et al.

(10) Patent No.: US 9,046,618 B2
(45) Date of Patent: Jun. 2, 2015

(54) SYSTEMS AND METHODS FOR SCANNING AN OBJECT WHILE AVOIDING RADIATION EXPOSURE

(75) Inventors: Gregor Hess, Wiesbaden (DE); Sven Wohlgethan, Wiesbaden (DE); Andreas Streyl, Seibersbach (DE); Joerg Bermuth, Rockenberg (DE); Urs Viehboeck, Darmstadt (DE); Patricia Schall, Weiterstadt (DE); Georg Geus, Wiesbaden (DE)

(73) Assignee: SMITHS HEIMANN GmbH, Wiesbaden (DE)

( * ) Notice: Subject to any disclaimer, the term of this patent is extended or adjusted under 35 U.S.C. 154(b) by 821 days.

(21) Appl. No.: 13/273,385

(22) Filed: Oct. 14, 2011

(65) Prior Publication Data
US 2012/0121070 A1 May 17, 2012

Related U.S. Application Data

(60) Provisional application No. 61/393,071, filed on Oct. 14, 2010.

(51) Int. Cl.
*A61B 6/10* (2006.01)
*G01V 5/00* (2006.01)
*H05G 1/54* (2006.01)
*G01T 7/12* (2006.01)

(52) U.S. Cl.
CPC .............. *G01V 5/0008* (2013.01); *H05G 1/54* (2013.01); *A61B 6/10* (2013.01); *G01T 7/12* (2013.01)

(58) Field of Classification Search
CPC ............ A61B 6/10; A61B 6/107; G01T 7/12; G01T 7/125; H05G 1/26; H05G 1/30; H05G 1/32; H05G 1/34; H05G 1/54
See application file for complete search history.

(56) References Cited

U.S. PATENT DOCUMENTS

| 4,008,396 | A | * | 2/1977 | Loyer ............................ 378/61 |
| 4,020,346 | A | | 4/1977 | Dennis |
| 4,357,535 | A | | 11/1982 | Haas |
| 6,031,890 | A | | 2/2000 | Bermbach et al. |
| 7,062,011 | B1 | * | 6/2006 | Tybinkowski et al. .......... 378/57 |
| 7,072,434 | B1 | * | 7/2006 | Tybinkowski et al. ............ 378/4 |
| 7,082,186 | B2 | * | 7/2006 | Zhao et al. ...................... 378/57 |
| 7,099,427 | B2 | * | 8/2006 | Cadwalader et al. ............. 378/4 |

(Continued)

FOREIGN PATENT DOCUMENTS

| EP | 2078957 | 7/2009 |
| JP | 9292472 | 11/1997 |

OTHER PUBLICATIONS

Keyence America, SL-V Series Safety Light Curtain Features Overview, as accessed on Nov. 6, 2012 from http://www.keyence.com/products/safety/safety/slv/slv_features_1.php.

(Continued)

*Primary Examiner* — Thomas R Artman
(74) *Attorney, Agent, or Firm* — Casimir Jones, S.C.

(57) ABSTRACT

The present invention provides system, devices, and methods for scanning an object while avoiding radiation exposure. For example, the present invention provides systems comprising a scanning device with input and output openings, and a safety sensor adjacent to the input or output opening that sends a signal that turns off or physically blocks electromagnetic radiation if the presence of an invading element (e.g., human hand) is detected by the safety sensor.

24 Claims, 5 Drawing Sheets

(56) References Cited

U.S. PATENT DOCUMENTS

| | | | |
|---|---|---|---|
| 7,099,434 B2* | 8/2006 | Adams et al. | 378/57 |
| 7,215,738 B2* | 5/2007 | Muenchau et al. | 378/57 |
| 2004/0175018 A1* | 9/2004 | MacArthur et al. | 382/103 |
| 2007/0133743 A1 | 6/2007 | Johnson et al. | |
| 2012/0121070 A1* | 5/2012 | Hess et al. | 378/117 |

OTHER PUBLICATIONS

Omron Scientific Technologies, Inc., F3SJ-E Safety Light Curtains, as accessed on Nov. 6, 2012 from http://www.sti.com/curtains/F3SJ-E/index.htm.

Phoenix Contact, Light Element—MSTB-LA/RD—1765690, as accessed on Nov. 6, 2012 from https://www.phoenixcontact.com/online/portal/us?uri=pxc-oc-itemdetail:pid=1765690&library=usen&tab=1.

Pinnacle Systems, Model PPG Perimeter Guarding Product Overview, as accessed on Nov. 8, 2012 from http://www.pinnaclesystems.com/mobile_site/Model-PPG-Product-Overview.html.

Rockwell Automation PAC GuardShield Type 4 Safety Light Curtains, as accessed on Nov. 6, 2012 from http://ab.rockwellautomation.com/Sensors-Switches/Operator-Safety/PAC-Type-4-GuardShield-Light-Curtains.

English Abstract of JP9292472, as accessed on Nov. 8, 2012 from http://worldwide.espacenet.com/publicationDetails/biblio?CC=JP&NR=9292472A&KC=A&FT=D&ND=3&date=19971111&DB=EPODOC&locale=en_EP.

International Search Report and Written Opinion for PCT Application No. PCT/IB2011/002883, mailed Apr. 11, 2012.

* cited by examiner

A.

B.

A.

B.

SYSTEMS AND METHODS FOR SCANNING AN OBJECT WHILE AVOIDING RADIATION EXPOSURE

CROSS-REFERENCE TO RELATED APPLICATIONS

The present application claims the benefit of U.S. Provisional Patent Application Ser. No. 61/393,071, filed Oct. 14, 2010, which is incorporated by reference in its entirety.

FIELD OF THE INVENTION

The present invention provides system, devices, and methods for scanning an object while avoiding radiation exposure. For example, the present invention provides systems comprising a scanning device with input and output openings, and a safety sensor adjacent to the input or output opening that sends a signal that turns off or physically blocks electromagnetic radiation if the presence of an invading element (e.g., human hand) is detected by the safety sensor.

BACKGROUND

Conventional X-ray inspection systems comprise a conveyor system (see, e.g., U.S. Pat. Pub. 20070133743, herein incorporated by reference). This system transports the objects through the scanning zone. At the entrance and the exit of the scanning zone there is flexible radiation shielding (e.g. lead curtains) which blocks X-ray radiation but allows the inspected objects to pass through. People can enter parts of their body through the flexible shielding which may cause exposure to X-ray radiation. To prevent this, conventional systems comprise additional casings or tunnels in front of the entrance/exit to cover the conveyor and to prevent access to the scanning zone.

SUMMARY OF THE INVENTION

The present invention provides system, devices, and methods for scanning an object while avoiding radiation exposure. For example, the present invention provides systems comprising a scanning device with input and output openings, and a safety sensor adjacent to the input or output opening that sends a signal that turns off or physically blocks electromagnetic radiation if the presence of an invading element (e.g., human hand) is detected by the safety sensor.

In certain embodiments, the present invention provides systems (or devices) for scanning an object while avoiding radiation exposure comprising: a) a scanning device that scans objects with electromagnetic radiation, wherein the scanning device comprises a housing component, wherein said housing component comprises input and output openings; and b) a first safety sensor adjacent to either the input opening or the output opening, wherein the first safety sensor sends a signal that turns off or physically blocks the electromagnetic radiation if: i) there is an object within the housing component being scanned by the electromagnetic radiation and, ii) the presence of an invading element is detected by the first safety sensor. In certain embodiments, wherein the scanning device does not have a guard component that would physically prevent human body parts from entering the housing component and being exposed to the electromagnetic radiation.

In particular embodiments, the present invention provides methods for scanning an object while avoiding radiation exposure comprising: a) providing a scanning system comprising: i) a scanning device with an input opening and an output opening; ii) a first safety sensor adjacent to either the input opening or the output opening, wherein the first safety sensor is in a non-scanning setting; b) placing an object on the scanning system such that it is in or enters the scanning device; and c) activating the scanning system such that: i) the scanning device scans the object with electromagnetic radiation; and ii) the first safety sensor switches to a scanning setting that allows the first safety sensor to send a signal to the scanning device that turns off or physically blocks the electromagnetic radiation if the presence of an invading element is detected by the first safety sensor.

In particular embodiments, the first safety sensor comprises an opto-electronic device. In further embodiments, the first safety sensor comprises a light curtain (e.g., from OMRON Scientific Technologies, Inc.). In certain embodiments, the electromagnetic radiation is selected from the group consisting of: radio-waves, microwaves, infrared radiation, ultraviolet radiation, X-rays and gamma rays. In further embodiments, the invading element is a portion of the human body (e.g., a human hand, human arm, human arm, human leg, human face, human head, etc.).

In particular embodiments, the systems further comprise a conveyor component that extends through the housing component and allows an object placed on the conveyor component to travel into the housing component via the input opening and out of the housing component via the output opening. In certain embodiments, the conveyor component comprises a conveyor belt or powered rollers.

In some embodiments, the systems further comprise a source component that emits electromagnetic radiation and is located inside the housing component. In other embodiments, the signal activates an aperture in front of the source component that physically prevents the electromagnetic radiation from entering the housing component.

In other embodiments, the signal turns the source component off such that it does not emit electromagnetic radiation. In further embodiments, the object is selected from the group consisting of: a brief case, a purse, a computer, a suitcase, baggage, cargo, goods, an umbrella, or a shoe.

In certain embodiments, the systems further comprise a first curtain attached to the housing component that substantially covers the input opening. In further embodiments, the first curtain comprises lead, plastic, or cloth. In other embodiments, the first safety sensor is positioned such that swinging of the first curtain is not detectable by the first safety sensor (e.g., the first curtain cannot swing far enough to be in the field of the sensor, or the curtain is made of a material that does not register with the first sensor). In other embodiments, the first safety sensor is positioned such that swinging of the first curtain is detectable, but the first safety sensor does not send the signal when the first curtain is detected (e.g., the curtain is composed of a material not detectable by the first safety sensor).

In some embodiments, the system further comprise a second safety sensor adjacent to either the input opening or the output opening, wherein the second safety sensor is not adjacent to the first safety sensor, and wherein the second safety sensor sends a signal that turns off or physically blocks the electromagnetic radiation if: i) there is an object within the housing component being scanned by the electromagnetic radiation and, ii) the presence of an invading element is detected by the second safety sensor. In certain embodiments, the systems further comprise a second curtain attached to the housing component that substantially covers the output opening. In other embodiments, the second curtain comprises lead, plastic, or cloth. In particular embodiments, the second safety sensor is positioned such that swinging of the second curtain is not detectable by the second safety sensor. In other embodiments, the second safety sensor is positioned such that swinging of the second curtain is detectable, but the second safety sensor does not send the signal when the second curtain is detected.

In particular embodiments, the systems further comprise a detector component capable of detecting electromagnetic radiation, wherein the detector component is located inside of the housing component. In further embodiments, the first safety sensor comprises a light curtain, wherein the light curtain comprises a plurality of photoelectric cells arranged in a row. In some embodiments, the systems further comprise a start scan button or switch that is designed to activate the system once the object is within the housing component. In other embodiments, the electromagnetic radiation comprises X-rays. In further embodiments, the systems further comprise a conveyor component configured to convey the object out the input opening if the signal is sent by the first safety sensor. In certain embodiments, the first and/or second safety sensor employs ultrasound detection. In further embodiments, the first and/or second safety sensor employs radar detection. In other embodiments, the first and/or second safety sensor is located outside of the housing component. In some embodiments, the first and/or second safety sensor is located inside of the housing component.

In some embodiments, the present invention provides systems (or devices) for scanning an object while avoiding radiation exposure comprising: a) a housing component having an input opening and an output opening, wherein the housing component is configured to contain electromagnetic radiation, b) a source component that emits electromagnetic radiation and is located inside the housing component, c) a detector component that detects electromagnetic radiation and is located inside the housing component, d) a conveyor component that extends through the housing component and allows an object placed on the conveyor component to travel into the housing component via the input opening and out of the housing component via the output opening, e) a first safety sensor adjacent to either the input opening or the output opening, wherein the first safety sensor sends a signal that prevents the source component from emitting electromagnetic radiation inside the housing component if: i) the source component is emitting electromagnetic radiation, ii) there is an object on the conveyor that is within the housing component, and iii) the presence of an invading element is detected by the first safety sensor.

In some embodiments, the present invention provides systems for scanning an object while avoiding radiation exposure comprising: a) a scanning device that scans objects with electromagnetic radiation, wherein the scanning device comprises a housing component having an input opening and an output opening; and b) a first non-physical barrier adjacent to either the input opening or the output opening, wherein the first non-physical barrier sends a signal that turns off or physically blocks the electromagnetic radiation if: i) there is an object within the housing component being scanned by the electromagnetic radiation and, ii) the presence of an invading element is detected by the first safety sensor. In particular embodiments, the first non-physical barrier comprises a first safety sensor.

In some embodiments, the present invention provides methods for modifying a scanning device comprising: a) providing: i) a scanning device with an input opening and an output opening, wherein the scanning device is configured to scan objects with electromagnetic radiation, and ii) a first safety sensor; b) attaching the first safety sensor to the scanning device adjacent to either the input opening or the output opening, wherein the first safety sensor is configured to send a signal to the scanning device that turns off or physically blocks the electromagnetic radiation if the presence of an invading element is detected by the first safety sensor.

DESCRIPTION OF THE FIGURES

FIG. 3A shows a side-view, FIG. 3C shows a top-view of the exemplary scanning device.

DETAILED DESCRIPTION OF THE INVENTION

The present invention provides system, devices, and methods for scanning an object while avoiding radiation exposure. For example, the present invention provides systems comprising a scanning device with input and output openings, and a safety sensor adjacent to the input or output opening that sends a signal that turns off or physically blocks electromagnetic radiation if the presence of an invading element (e.g., human hand) is detected by the safety sensor. In general, the present invention prevents persons from entering parts of the body (e.g. arms or hands) into a X-ray system or other object scanning system so any potentially dangerous irradiation can be avoided.

Figure 1:
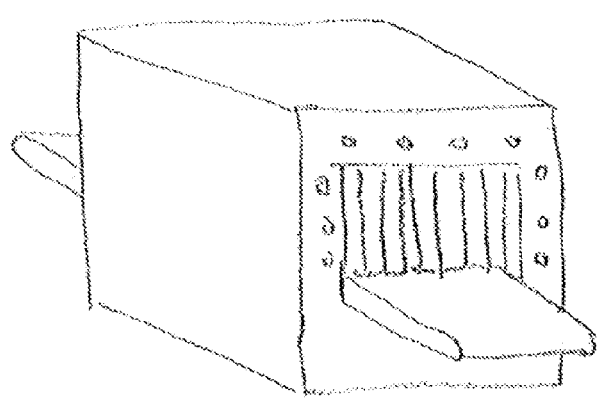
FIG. 1A shows an exemplary scanning device with a plurality of safety sensors located around an input opening (the input opening is shown with a curtain covering the opening).
FIG. 1B shows an exemplary scanning device with a safety sensor (hatched lines) in the shape of a rectangle extending over a portion of the conveyor component.
Figure 1:
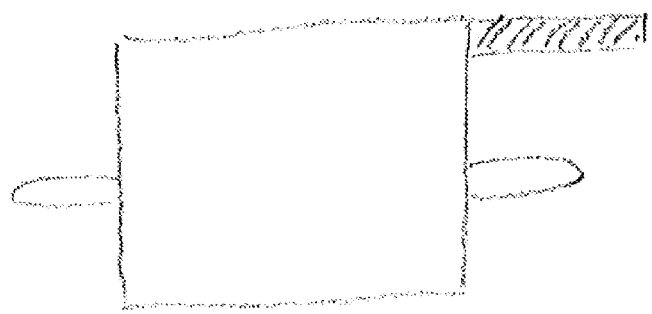
Figure 2:
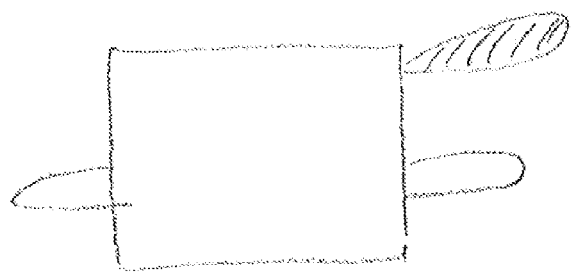
FIG. 2A shows an exemplary scanning device with a safety sensor (hatched lines) in the shape of a fan blade extending over the conveyor component.
FIG. 2B shows an exemplary scanning device with a safety sensor (dashed line) in the shape of a straight line extending over the conveyor component.
Figure 2:
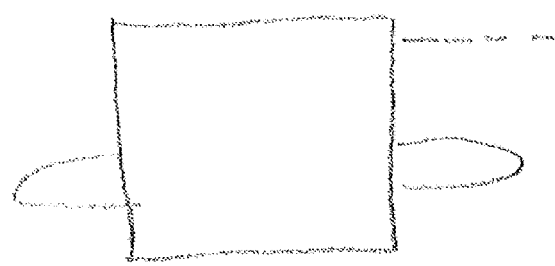
Figure 3:
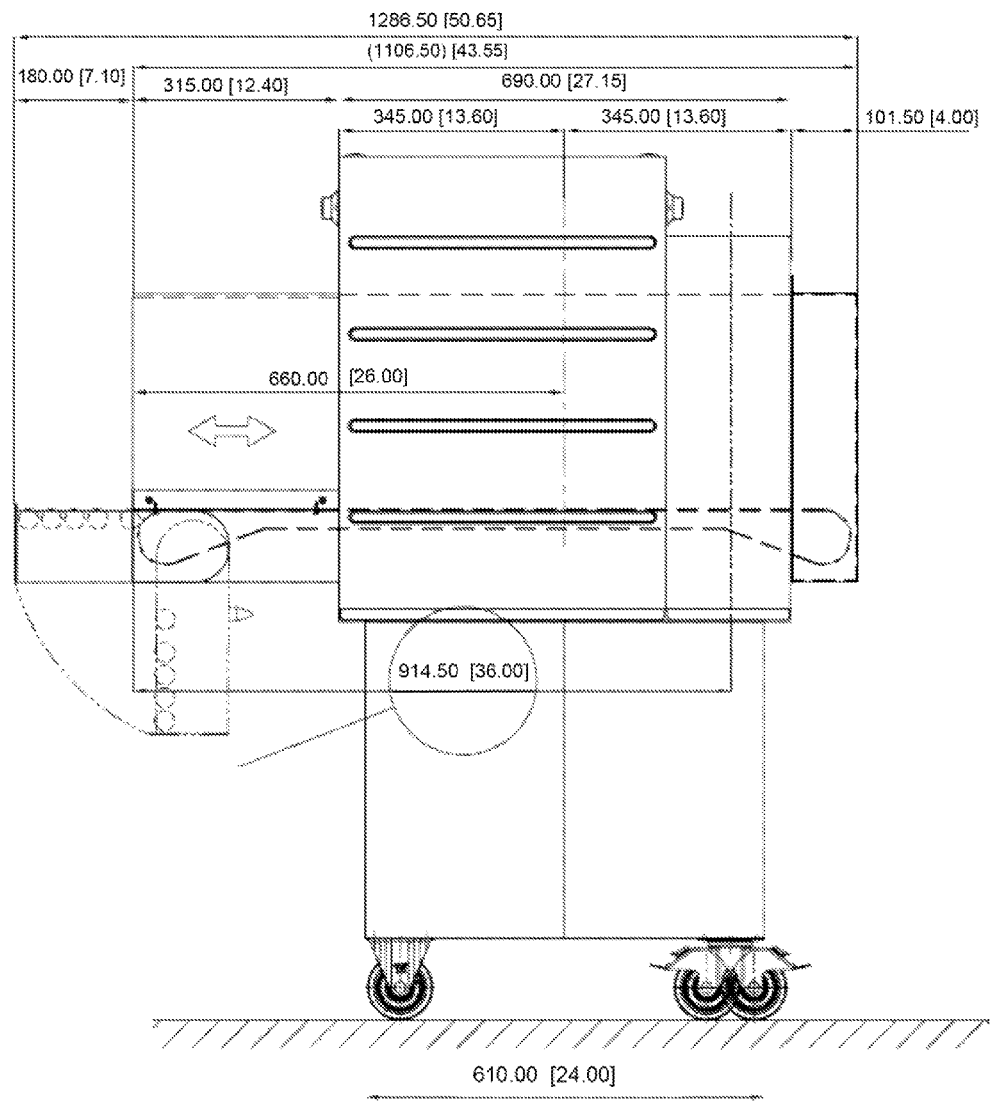
FIG. 3 shows three views of an exemplary scanning device that does not have a casing, tunnel, or other guard in front of the input opening to prevent accidental exposure to radiation.
Figure 3B:
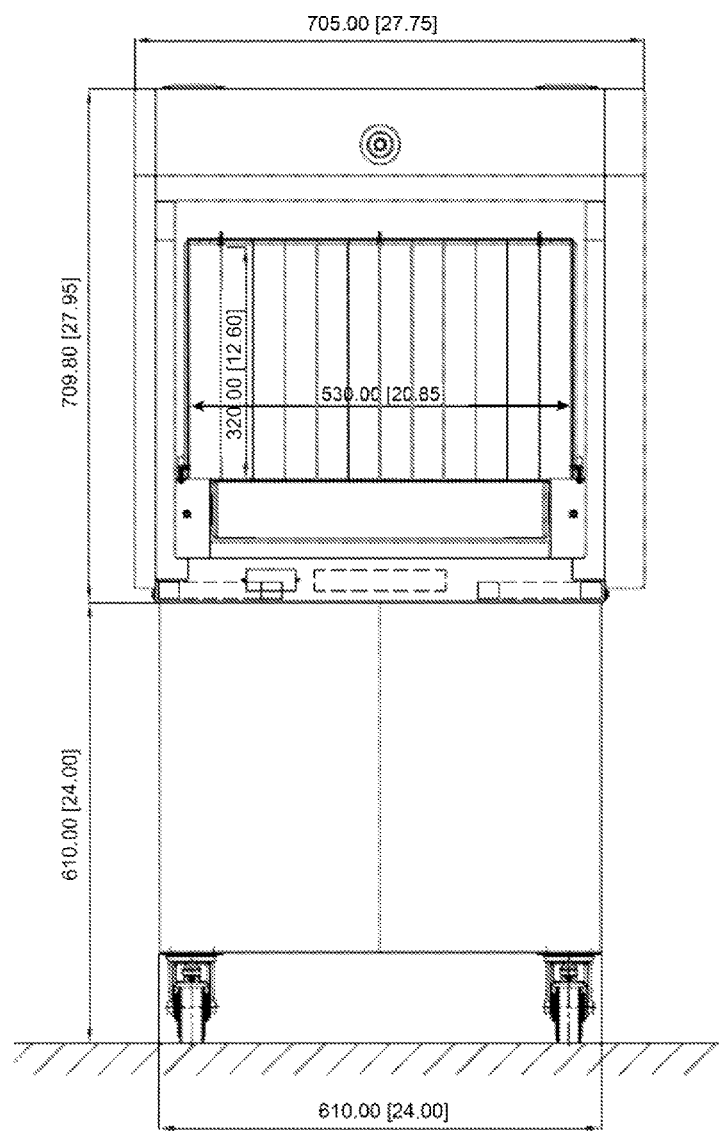
FIG. 3B shows a front-view.
Figure 3:
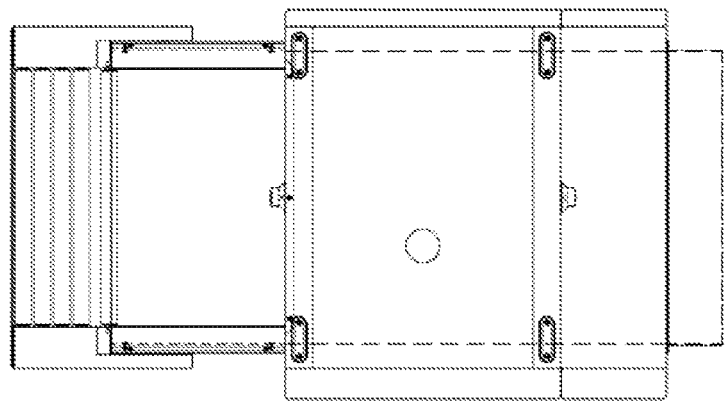

In certain embodiments, one or more safety sensors are attached to or near the entrance and/or the exit of a scanning device (e.g., the device shown in FIGS. 1-3 or those shown in U.S. Pat. Pub. 20070133743). These safety sensors detect if something approaches the scanning zone which is not the object to be inspected.

The surveillance distance of the safety sensors is not limited and may be adjustable. If something enters the surveillance zone created by the safety sensor(s), safety measures will be activated (e.g., close shutter, shut down of X-ray generator, etc.). In particular embodiments, the safety sensor can be, for example, ultrasound sensors (e.g., like in park distance control systems), radar sensors or light barriers.

In certain embodiments, the safety sensor is a light curtain. A light curtain is generally a device made of several photoelectric cells in a row creating a 'light curtain,' which can trigger an action if the 'curtain' is blocked. Exemplary light curtains are manufactured by various companies including, for example, Rockwell Automation (GUARDSHIELD), Keyence America (SL series), Pinnacle Systems (e.g., model PPG), Phoenix Contact, and OMRON Scientific Technologies, Inc. (e.g., F3SJ).

In an exemplary embodiment, the operational flow of employing a scanning device with a safety sensor may be as follows. First, an object to be scanned is placed through the area detected by the sensor (e.g., light curtain) onto the conveyor—but the sensor is not yet activated so it does not send a shut down signal. Next, the 'start scan' key is pressed. Then, the object is scanned and moves all the way to the (closed) end of the inspection tunnel. If during the scan something blocks the sensor (e.g., light curtain) such as a hand, then the scan will be stopped (e.g., very quickly or instantly) and the X-ray or other electromagnetic radiation will be cut off. The object can then be automatically conveyed back to the entry side of the inspection tunnel.

All publications and patents mentioned in the present application are herein incorporated by reference. Various modification and variation of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A system for scanning an object while avoiding radiation exposure comprising:
   a) a scanning device that scans objects with electromagnetic radiation, wherein said scanning device comprises a housing component having an input opening and an output opening; and
   b) a first safety sensor adjacent to either said input opening or said output opening, wherein said first safety sensor sends a signal that turns off or physically blocks said electromagnetic radiation if: i) there is an object within said housing component being scanned by said electromagnetic radiation and, ii) an invading element is detected by said first safety sensor approaching said input opening or said output opening.

2. The system of claim 1, wherein said first safety sensor comprises an opto-electronic device.

3. The system of claim 1, wherein said first safety sensor comprises a light curtain.

4. The system of claim 1, wherein said electromagnetic radiation is selected from the group consisting of: radiowaves, microwaves, infrared radiation, ultraviolet radiation, X-rays, and gamma rays.

5. The system of claim 1, wherein said invading element is a portion of the human body.

6. The system of claim 1, wherein said invading element comprises a human hand.

7. The system of claim 1, further comprising a conveyor component that extends through said housing component and allows an object placed on said conveyor component to travel into said housing component via said input opening and out of said housing component via said output opening.

8. The system of claim 1, further comprising a source component that emits electromagnetic radiation and is located inside said housing component.

9. The system of claim 8, wherein said signal activates an aperture in front of said source component that physically prevents said electromagnetic radiation from entering said housing component.

10. The system of claim 8, wherein said signal turns said source component off such that it does not emit electromagnetic radiation.

11. The system of claim 1, further comprising a first curtain attached to said housing component that substantially covers said input opening.

12. The system of claim 11, wherein said first safety sensor is positioned such that swinging of said first curtain is not detectable by said first safety sensor.

13. The system of claim 11, wherein said first safety sensor is positioned such that swinging of said first curtain is detectable, but said first safety sensor does not send said signal when said first curtain is detected.

14. The system of claim 1, further comprising a second safety sensor adjacent to either said input opening or said output opening, wherein said second safety sensor is not adjacent to said first safety sensor, and wherein said second safety sensor sends a signal that turns off or physically blocks said electromagnetic radiation if: i) there is an object within said housing component being scanned by said electromagnetic radiation and, ii) the presence of an invading element is detected by said second safety sensor.

15. The system of claim 14, further comprising a second curtain attached to said housing component that substantially covers said output opening.

16. The system of claim 15, wherein said second safety sensor is positioned such that swinging of said second curtain is not detectable by said second safety sensor.

17. The system of claim 15, wherein said second safety sensor is positioned such that swinging of said second curtain is detectable, but said second safety sensor does not send said signal when said second curtain is detected.

18. The system of claim 1, further comprising a detector component capable of detecting electromagnetic radiation, wherein said detector component is located inside of said housing component.

19. The system of claim 1, wherein said first safety sensor comprises a light curtain, wherein said light curtain comprises a plurality of photoelectric cells arranged in a row.

20. The system of claim 1, further comprising a start scan button or switch that is designed to activate said system once said object is within said housing component.

21. The system of claim 1, further comprising a conveyor component configured to convey said object out said input opening if said signal is sent by said first safety sensor.

22. The system of claim 1, wherein said first safety sensor is located outside of said housing component.

23. A system for scanning an object while avoiding radiation exposure comprising:
   a) a housing component having an input opening and an output opening, wherein said housing component is configured to contain electromagnetic radiation,
   b) a source component that emits electromagnetic radiation and is located inside said housing component,
   c) a detector component that detects electromagnetic radiation and is located inside said housing component,
   d) a conveyor component that extends through said housing component and allows an object placed on said conveyor component to travel into said housing component via said input opening and out of said housing component via said output opening,
   e) a first safety sensor adjacent to either said input opening or said output opening, wherein said first safety sensor sends a signal that prevents said source component from emitting electromagnetic radiation inside said housing component if:
      i) said source component is emitting electromagnetic radiation,
      ii) there is an object on said conveyor that is within said housing component, and
      iii) an invading element is detected by said first safety sensor approaching said input opening or said output opening.

24. A method for scanning an object while avoiding radiation exposure comprising:
  a) providing a scanning system comprising:
    i) a scanning device with an input opening and an output opening;
    ii) a first safety sensor adjacent to either said input opening or said output opening, wherein said first safety sensor is in a non-scanning setting;
  b) placing an object on said scanning system such that it is in or enters said scanning device; and
  c) activating said scanning system such that:
    i) said scanning device scans said object with electromagnetic radiation; and
    ii) said first safety sensor switches to a scanning setting that allows said first safety sensor to send a signal to said scanning device that turns off or physically blocks said electromagnetic radiation if an invading element is detected by said first safety sensor approaching said input opening or said output opening.

* * * * *